United States Patent [19]

Cosgrove et al.

[11] Patent Number: 5,194,640

[45] Date of Patent: Mar. 16, 1993

[54] PROCESS FOR MAKING HIGH-PURITY OLEIC ACID

[75] Inventors: John P. Cosgrove, Charleston; J. George Hayden, Awendaw; Philip L. Robinson, Isle of Palms, all of S.C.

[73] Assignee: Westvaco Corporation, New York, N.Y.

[21] Appl. No.: 712,717

[22] Filed: Jun. 10, 1991

[51] Int. Cl.$^5$ ............................................. C11C 3/14
[52] U.S. Cl. ................................. 554/126; 554/162; 554/174; 530/233
[58] Field of Search ............................ 260/405.5, 419; 530/233

[56] References Cited

U.S. PATENT DOCUMENTS

| | | | |
|---|---|---|---|
| 2,343,644 | 3/1944 | Cawley | 260/405.6 |
| 2,421,157 | 5/1947 | Myers et al. | 260/419 |
| 2,450,235 | 9/1958 | Gee | 260/428.5 |
| 2,838,480 | 6/1958 | Swern et al. | 260/96.5 |
| 3,162,658 | 12/1964 | Baltes et al. | 260/405.6 |
| 3,753,968 | 8/1973 | Ward | 260/97.6 |
| 3,755,389 | 8/1973 | Blaney | 260/419 |
| 3,923,768 | 12/1979 | Powers | 530/233 |
| 3,953,484 | 4/1976 | Sutker | 260/419 |
| 4,097,507 | 6/1978 | Person | 260/413 |
| 4,156,095 | 5/1979 | Jeune et al. | 562/509 |
| 4,529,551 | 7/1985 | Cleary et al. | 260/419 |
| 4,534,900 | 8/1985 | Cleary | 260/428.5 |

OTHER PUBLICATIONS

Chemical Abstracts, vol. 84, #9, p. 449, 1976 68653r.
"Polymerization, Copolymerization, and Isomerization", J. C. Cowan, *The Journal of the American Oil Chemicals Society*, vol. 31, Nov. 1954, pp. 529–535.

*Primary Examiner*—José G. Dees
*Assistant Examiner*—Deborah D. Carr
*Attorney, Agent, or Firm*—Daniel B. Reece, IV; Terry B. McDaniel; Richard L. Schmalz

[57] ABSTRACT

An oleic acid containing adduct is produced by reacting tall oil fatty acid (which contains pre-conjugated linoleic acid) with a dienophile at a temperature between 180° C. and 300° C. No catalyst or solvent is necessary for the reaction to occur. The adduct is subsequently distilled to yield a high-purity, light color oleic acid.

4 Claims, No Drawings

PROCESS FOR MAKING HIGH-PURITY OLEIC ACID

FIELD OF THE INVENTION

This invention relates to the production of high-purity oleic acid. In particular, this invention relates to a novel process for making a high-purity, light color oleic acid from tall oil fatty acid.

BACKGROUND OF THE INVENTION

A number of applications have been developed for oleic acid in the fields of cosmetics, textiles, metalworking chemicals, and corrosion inhibitors. As used herein the term "oleic acid" is intended to mean a cis-9-octadecenoic acid; a monounsaturated $C_{18}$ fatty acid which is a common component of almost all naturally occurring fats as well as tall oil. Currently, most commercial oleic acid is derived from animal tallow or natural vegetable oils.

Tall oil consists of a mixture of fatty acids, resin acids, and various neutral components (e.g., hydrocarbons, resin and wax alcohols, sterols, esters, and residues). About 40 to 50% of the fatty acids contained in tall oil is oleic acid, while another 35 to 45% is linoleic acid (9,11- or 9,12-octadecadienoic acid). It has been known to fractionally distill tall oil since the early 1900's. However, due to the structural similarities between oleic acid and linoleic acid, additional refining steps have been necessary to separate (and purify) these two acids.

One such separation method is the Emersol process described in U.S. Pat. No. 2,421,157 to Myers et. al., which uses methanol as a solvent. The fatty acid source is mixed with anhydrous methanol and the subsequent solution is subjected to low temperatures and filtered to extract the oleic acid. A similar solvent process is taught by Gee in U.S. Pat. No. 2,450,235 where acetone is employed as a solvent in place of methanol. Both of these processes depend on $NH_3$ refrigeration to cool the solvent fatty acid mixture and can be very costly.

Another method of producing oleic acid is based on the use of molecular sieves to separate the different fatty acids, as evidenced by U.S. Pat. Nos. 4,529,551 to Cleary et al., and 4,534,900 to Cleary. Two of the drawbacks to these processes are the need to use two solvents for the separation and the problem of the molecular sieve "filter" becoming clogged with trace contaminants.

Other known methods of separating oleic acid include: a methyl formate solvent process (U.S. Pat. No. 3,755,389 to Blaney), an air entrainment process (U.S. Pat. No. 3,953,484 to Sutker), a lithium soap separation process (U.S. Pat. No. 4,097,507 to Person), and a urea separation process (U.S. Pat. No. 2,838,480 to Swern et al.). Although promising, none of these processes has yet been commercialized on a major scale.

Therefore, it is the object of this invention to provide a process for producing high-purity, light color oleic acid. Other objects, features, and advantages will be evident from the following disclosure.

SUMMARY OF THE INVENTION

The object of this invention is met by complexing the linoleic portion of the tall oil fatty acid mixture, thereby allowing the oleic acid portion to be isolated in a very pure form (i.e., at least 92% pure). Herein, the term complexing refers to the procedure of first conjugating (via a strong base) the double bonds of the linoleic acid fraction and subsequently reacting this conjugated product with a dienophile to increase the molecular weight relative to the original linoleic acid and oleic acid. This increase in molecular weight results in a significant difference in the boiling points and allows the separation of the oleic acid from the residual linoleic acid adduct. As a result, a very high-purity, light color oleic acid can be isolated via distillation.

DESCRIPTION OF THE PREFERRED EMBODIMENT

The novel process that yields a high-purity oleic acid reacts a dienophile with the base-conjugated linoleic acid portion of the tall oil fatty acid mixture at elevated temperatures. The resulting reaction mixture is subsequently distilled to yield an oleic acid substantially free of impurities.

It is recognized in the art that several processes are known for conjugating linoleic acid, as shown in U.S. Pat. Nos. 2,343,644 to Cawley and 3,162,658 to Baltes et al., which are hereby incorporated by reference. The method chosen to conjugate the linoleic acid portion of the tall oil fatty acid mixture must employ a base, and will depend upon cost considerations, the desired conversion, and other factors.

It is known in the art to react conjugated linoleic acid in the presence of a catalyst with certain dienophiles to produce Diels-Alder adducts. It is also known that the reactivity of the conjugated linoleic acid is determined by its geometrical isomerism about the double-bond system; and that the preferred reactive isomer has a trans-trans configuration. As demonstrated by the article, "Polymerization, Copolymerization, and Isomerization", J. C. Cowan, The Journal of the American Oil Chemicals Society, Vol. 31, November 1954, pp. 529-535, it has long been taught that the use of catalysts (such as crystalline clay, iodine, sodium or potassium bisulfates, sulfur, selenium, noble metals, and the like) to isomerize the cis-trans isomers into the trans-trans state is necessary to induce these cis-trans isomers of conjugated linoleic acid to react in a Diels-Alder reaction.

The process of reacting conjugated linoleic acid in the presence of a catalyst with dienophiles to produce Diels-Alder adducts has traditionally been used to make $C_{21}$ dicarboxylic acids. Examples of this are found in U.S. Pat. Nos. 3,753,968 to Ward (which uses iodine as a catalyst) and 4,156,095 to Jeune et al. (which employs crystalline clay).

However, catalysts cannot productively be used in the manufacture of oleic acid due to the fact that there are two isomers of monounsaturated $C_{18}$ fatty acid. Oleic acid, the cis-isomer, exists as a liquid at room temperature (i.e., it has a melting point of 13.2° C.). The trans-isomer, elaidic acid, exists as a white solid at room temperature (i.e., it has a melting point of 43.7° C.). As the trans-isomer, elaidic acid is thermodynamically more stable than oleic acid. Thus, any use of a catalyst to generate oleic acid will instead produce large portions of elaidic acid (until equilibrium is reached wherein the majority of the mixture will be elaidic acid).

Likewise, any attempt to convert linoleic acid to oleic acid via partial hydrogenation will result primarily in the production of the trans-isomer elaidic acid, with very little oleic acid being formed.

By employing a strong base the applicants' process conjugates the linoleic acid portion of the tall oil fatty acid mixture without affecting the oleic acid portion. Subsequently, the dienophile is added (to react with the conjugated linoleic acid) in an amount up to about 26% by weight of the fatty acid. While adding the dienophile at the beginning of the reaction gave good results, it is preferred to meter the addition over a period of at least two hours (depending on the dienophile).

Dienophiles which are suitable for use in this reaction are of the form:

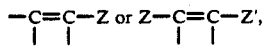

where Z and Z' are H, CHO, COR, COOH, COOR, COCl, COAr, CN, $NO_2$, Ar, $CH_2OH$, $CH_2Cl$, $CH_2NH_2$, $CH_2CN$, $CH_2COOH$, R, halogen, or C≡C. As used herein, R represents an alkyl group (a saturated hydrocarbon group) and Ar represents an aryl group (an aromatic hydrocarbon group). The structure C=C represents an alkene group with hydrogens attached. These include: acrylic acid, maleic acid, maleic anhydride, fumaric acid, methylacrylate, acrylonitrile, acrolein, dimethylacetylene-dicarboxylate, vinyl sulfonic acid or esters, alkyl maleimides, and the like.

The conjugated linoleic acid is reacted with the chosen dienophile to yield an increased molecular weight Diels-Alder adduct at a temperature range between 180° C. and 300° C. The preferred temperature for the reaction is around 230° C. to 260° C. for a period of between two to four hours. Thus, the applicants' process uses elevated temperature in place of traditional catalysts to thermally isomerize the conjugated cis-trans linoleic acid into the trans-trans form. This thermal treatment does not result in any appreciable isomerization of oleic acid into elaidic acid.

At the end of the reaction, the reaction mixture consists of oleic acid and a mixture of $C_{36}$ thermal dimers and $C_{21}$ dicarboxylic acids. This reaction mixture is subsequently distilled at a temperature range of 210° C. to 220° C. under vacuum to remove the substantially pure oleic acid. Several viable methods of distillation are known and can be used including fractional distillating columns and wiped-film evaporators.

The following examples are provided to further illustrate the present invention and are not to be construed as limiting the invention in any manner.

EXAMPLE 1

To a 1 L Parr reactor equipped with a stirrer was charged 500 g of PAMOLYN® 380 fatty acid. (PAMOLYN® 380 is a tall oil derived fatty acid containing 69% conjugated linoleic acid, sold by Hercules Incorporated.) The fatty acid was heated, with stirring, to a final temperature of 240° C. When the temperature of the Parr reactor reached 180° C., the addition of 130 g of acrylic acid was begun. The acrylic acid was pumped into the Parr reactor via a Milton Roy pump at the rate of 92 ml per hour, until all 130 g of acrylic acid had been added. Once the top temperature of 240° C. was obtained, the reaction was maintained at this temperature for four hours, generating a maximum pressure of 70 psi. At the end of the reaction, the reaction mixture consisted of 25-30% oleic acid and 65-75% $C_{36}$ thermal dimers and $C_{21}$ dicarboxylic acids.

The resultant oleic acid reaction mixture was purified on a two-inch Pope wiped-film evaporator (WFE). The distillation, preformed at a temperature of 200° C. and a pressure of less than 0.1 mm of Hg., resulted in a yield of about 100 grams of high-purity oleic acid having a Gardner Color of 1.

EXAMPLE 2

Two reactions were run where the percent by weight of the acrylic acid, based on the weight of fatty acid, was varied.

Each of two 1 L Parr reactors (equipped with stirrers) were charged separately with 600 g of conjugated L-1 fatty acid. (L-1 is a tall oil derived fatty acid containing roughly equivalent amounts of oleic and linoleic acid, and less that 1% rosin acid, made by Westvaco, Inc.). The fatty acid was heated, with stirring, to a final temperature of 250° C. When the temperatures of the Parr reactors reached 180° C., the two respective additions of acrylic acid were begun. The respective amounts of acrylic acid were pumped into the Parr reactors via Milton Roy pumps at the rate of 92 ml per hour, until all the acrylic acid had been added. The top temperature of 250° C. was maintained for four hours, generating a maximum of 70 psi. The results are listed in Table I below.

TABLE I

| Run # | Amount Acrylic Acid* | Monomeric Fatty Acid Yield** |
|---|---|---|
| 1 | 12.5% | 58.7% |
| 2 | 15.0% | 61.4% |

*Weight percent acrylic acid, based on weight of fatty acid.
**Yields are based on gas chromatography.

The oleic acid purification was done on a two-inch glass, laboratory WFE. Distillation was performed at 0.1 mm Hg at a temperature of 210° C. to 220° C. This produced high-purity oleic acid as a heads cut. The results are listed in Table II below.

TABLE II

| | WFE Yields* | | Oleic Acid** | |
|---|---|---|---|---|
| Run # | Oleic Acid Heads | Bottoms | Purity | Gardner Color |
| 1 | 48.3 | 48.1 | 82 | 1 |
| 2 | 55.3 | 44.7 | 75 | 1 |

*Yields are based on weight of each fraction obtained versus total weight of reaction mixture.
**Purity based on GC analysis with no correction for response factors.

Many modifications and variations of the present invention will be apparent to one of ordinary skill in the art in light of the above teaching. It is understood therefore that the scope of the invention is not to be limited by the foregoing description but rather is to be defined by the claims appended hereto.

What is claimed is:

1. A process for the production of oleic acid, comprising:
    (a) reacting in a cycloaddition reaction 100 parts by weight of a tall oil fatty acid mixture containing conjugated linoleic acid, in the absence of a catalyst, with
    (b) from 1 to 26 parts by weight of a dienophile,
    (c) at a temperature between 180° C. to 300° C. for a period of 0.5 to 12.0 hours to produce a linoleic acid containing adduct, and
    (d) distilling and recovering the oleic acid fraction from the said adduct.

2. The process of claim 1 wherein said dienophile is selected from the group consisting of:

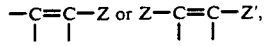

where Z and Z' are H, CHO, COR, COOH, COOR, COCl, COAr, CN, $NO_2$, Ar, $CH_2OH$, $CH_2Cl$, $CH_2NH_2$, $CH_2CN$, $CH_2COOH$, R, halogen, or C≡C.

3. The process of claim 1 wherein said dienophile is selected from the group consisting of acrylic acid, maleic acid, maleic anhydride, fumaric acid, methylacrylate, acrylonitrile, acrolein, dimethylacetylene-dicarboxylate, vinyl sulfonic acid or esters, or alkyl maleimides.

4. The process of claim 1 wherein said cycloaddition reaction is carried out at a temperature between 230° C. and 260° C. for a period of 1 to 4 hours.

* * * * *